(12) United States Patent
Najarian et al.

(10) Patent No.: US 9,339,241 B2
(45) Date of Patent: May 17, 2016

(54) ASSESSMENT AND PREDICTION OF CARDIOVASCULAR STATUS DURING CARDIAC ARREST AND THE POST-RESUSCITATION PERIOD USING SIGNAL PROCESSING AND MACHINE LEARNING

(75) Inventors: Kayvan Najarian, Northville, MI (US); Sharad Shandilya, Richmond, VA (US); Kevin R. Ward, Superior Township, MI (US)

(73) Assignee: Virginia Commonwealth University, Richmond, VA (US)

( * ) Notice: Subject to any disclaimer, the term of this patent is extended or adjusted under 35 U.S.C. 154(b) by 407 days.

(21) Appl. No.: 14/353,736

(22) PCT Filed: May 25, 2012

(86) PCT No.: PCT/US2012/039502
§ 371 (c)(1),
(2), (4) Date: Nov. 17, 2014

(87) PCT Pub. No.: WO2012/166568
PCT Pub. Date: Dec. 6, 2012

(65) Prior Publication Data
US 2015/0065815 A1    Mar. 5, 2015

Related U.S. Application Data

(60) Provisional application No. 61/490,827, filed on May 27, 2011.

(51) Int. Cl.
*A61B 5/00* (2006.01)
*A61N 1/37* (2006.01)
(Continued)

(52) U.S. Cl.
CPC .............. *A61B 5/7267* (2013.01); *A61B 5/0205* (2013.01); *A61B 5/0402* (2013.01);
(Continued)

(58) Field of Classification Search
CPC .. A61B 5/0402; G06F 19/3437; G06F 19/345
See application file for complete search history.

(56) References Cited

U.S. PATENT DOCUMENTS 7,593,772 B2 * 9/2009 Sherman .............. A61N 1/3925
600/518
2004/0230105 A1  11/2004 Geva et al.
(Continued)

FOREIGN PATENT DOCUMENTS

WO    WO 2010077997 A2 *  7/2010  ........... A61B 5/0205

OTHER PUBLICATIONS

Becker et al., Outcome of CPR in a large metropolitan area—where are the survivors?, Ann. Emerg. Med., 20(4):355-61 (1991).
(Continued)

*Primary Examiner* — Gary Jackson
*Assistant Examiner* — Amanda Steinberg
(74) *Attorney, Agent, or Firm* — Marshall, Gerstein & Borun LLP (57) ABSTRACT

Real-time, short-term analysis of ECG, by using multiple signal processing and machine learning techniques, is used to determine counter shock success in defibrillation. Combinations of measures when used with machine learning algorithms readily predict successful resuscitation, guide therapy and predict complications. In terms of guiding resuscitation, they may serve as indicators and when to provide counter shocks and at what energy levels they should be provided as well as to serve as indicators of when certain drugs should be provided (in addition to their doses). For cardiac arrest, the system is meant to run in real time during all current resuscitation procedures including post-resuscitation care to detect deterioration for guiding care such as therapeutic hypothermia.

6 Claims, 9 Drawing Sheets

(51) Int. Cl.
| | |
|---|---|
| A61B 5/083 | (2006.01) |
| G06F 19/00 | (2011.01) |
| A61B 5/0452 | (2006.01) |
| A61B 5/0205 | (2006.01) |
| A61B 5/04 | (2006.01) |
| A61B 5/053 | (2006.01) |
| A61B 5/1455 | (2006.01) |
| A61B 5/0402 | (2006.01) |
| A61N 1/39 | (2006.01) |

(52) U.S. Cl.
CPC .......... *A61B5/04017* (2013.01); *A61B 5/0452* (2013.01); *A61B 5/14551* (2013.01); *A61B 5/486* (2013.01); *A61B 5/4836* (2013.01); *A61B 5/7203* (2013.01); *A61B 5/726* (2013.01); *G06F 19/3406* (2013.01); *A61B 5/053* (2013.01); *A61B 5/0836* (2013.01); *A61B 5/725* (2013.01); *A61B 2505/01* (2013.01); *A61N 1/3925* (2013.01); *G06F 19/3437* (2013.01)

(56) References Cited

U.S. PATENT DOCUMENTS

| | | | |
|---|---|---|---|
| 2005/0256415 A1 | 11/2005 | Tan et al. | |
| 2007/0129647 A1* | 6/2007 | Lynn | A61B 5/00 600/538 |
| 2009/0069703 A1* | 3/2009 | Takla | A61B 5/0402 600/509 |
| 2011/0190650 A1* | 8/2011 | McNair | A61B 5/00 600/518 |
| 2012/0123232 A1* | 5/2012 | Najarian | A61B 5/0022 600/345 |

OTHER PUBLICATIONS

Berg et al., Part 5: adult basic life support: 2010 American Heart Association Guidelines for Cardiopulmonary Resuscitation and Emergency Cardiovascular Care, Circulation, 122(18 Suppl 3):S685-705 (2010).
Box et al., Shock outcome prediction before and after CPR: a comparative study of manual and automated active compression-decompression CPR, Resuscitation, 78(3):265-74 (2008).
Eilevstjonn et al., Shock outcome is related to prior rhythm and duration of ventricular fibrillation, Resuscitation 75(1):60-7 (2007).
Gundersen et al., Identifying approaches to improve the accuracy of shock outcome prediction for out-of-hospital cardiac arrest, Resuscitation, 76(2):279-84 (2008).
Guyon et al., Gene selection for cancer classification using support vector machines, Machine Learning, 46:389-422 (2002).
International Preliminary Report on Patentability, International Application No. PCT/US2012/039502, dated Dec. 2, 2013.
International Search Report and Written Opinion, International Application No. PCT/US2012/039502, dated Nov. 28, 2012.
Kohavi et al., Wrappers for feature subset selection, Artificial Intelligence, 97:273-324 (1997).
Little et al., Exploiting Nonlinear Recurrence and Fractal Scaling Properties for Voice Disorder Detection, Biomed. Engineer. Online, 6:23 (2007).
Nadkarni et al., First documented rhythm and clinical outcome from in-hospital cardiac arrest among children and adults, JAMA, 295(1):50-7 (2006).
Neurauter et al., Prediction of countershock success using single features from multiple ventricular fibrillation frequency bands and feature combinations using neural networks, Resuscitation, 73(2):253-63 (2007).
Nichol et al., Regional variation in out-of-hospital cardiac arrest incidence and outcome, JAMA, 300(12):1423-31 (2008).
Ristagno et al., Prediction of successful defibrillation in human victims of out-of-hospital cardiac arrest: a retrospective electrocardiographic analysis, Anaesth. Intensive Care, 36(1):46-50 (2008).
Savitzky et al., Smoothing and differentiation of data by simplified least squares procedures, Anal. Chem., 36(8):1627-39 (1964).
Shandilya et al., Predicting defibrillation success with a multiple-domain model using machine learning, Proc. 2011 IEEE/ICME (International Complex Medical Engineering), pp. 9-14 (May 22-25, 2011).
Shandilya et al., Prediction of shock outcome using signal processing machine learning, Circulation, 122:A242 (2010).
Strohmenger, Predicting defibrillation success, Curr. Opin. Crit. Care, 14(3):311-6 (2008).
Valenzuela et al., Estimating effectiveness of cardiac arrest interventions: a logistic regression survival model, Circulation, 96(10):3308-13 (1997).
Watson et al., Improved prediction of defibrillation success for out-of-hospital VF cardiac arrest using wavelet transform methods, Resuscitation, 63(3):269-75 (2004).
Watson et al., Practical issues in the evaluation of methods for the prediction of shock outcome success in out-of-hospital cardiac arrest patients, Resuscitation, 68(1):51-9 (2006).
Weisfeldt et al., Resuscitation after cardiac arrest: a 3-phase time-sensitive model, JAMA, 288(23):3035-8 (2002).
Weiss et al., The dynamics of cardiac fibrillation, Circulation, 112(8):1232-40 (2005).
Zaitsev et al., Distribution of excitation frequencies on the epicardial and endocardial surfaces of fibrillating ventricular wall of the sheep heart, Circ. Res., 86(4):408-17 (2000).

* cited by examiner

ASSESSMENT AND PREDICTION OF CARDIOVASCULAR STATUS DURING CARDIAC ARREST AND THE POST-RESUSCITATION PERIOD USING SIGNAL PROCESSING AND MACHINE LEARNING

CROSS REFERENCE TO RELATED APPLICATION

The present application claims benefit of provisional U.S. Patent Application Ser. No. 61/490,827 filed May 27, 2011.

BACKGROUND OF THE INVENTION

1. Field of the Invention

The present invention generally relates to a novel method for analyzing the Electrocardiogram (ECG) and other physiologic signals of Ventricular Fibrillation (VF) in order to identify and capitalize on the optimum physiologic moments when resuscitation is most likely and also to guide therapy by making therapeutic recommendations as well as predicting rearrest. More particularly, the invention is an integrative model that performs real-time, short-term analysis of ECG through machine learning techniques.

2. Background Description

Sudden cardiac death is a significant public health concern and a leading cause of death in many parts of the world. In the United States cardiac arrest claims greater than 300,000 lives annually. Survival rates for out-of-hospital cardiac arrest remain dismal (cf. G. Nichol, E. Thomas, C. W. Callaway, et al., "Regional variation in out-of-hospital cardiac arrest incidence and outcome", *J Am Med Assoc* 2008; 300:1423-1431). Ventricular Fibrillation (VF) is the initially encountered arrhythmia in 20-30% of cardiac arrest cases (cf. V. M. Nadkarni, G. L. Larkin, M. A. Peberdy, S. M. Carey, W. Kaye, M. E. Mancini, G. Nichol, T. Lane-Truitt, J. Potts, J. P. Ornato, and R. A. Berg. "First documented rhythm and clinical outcome from in-hospital cardiac arrest among children and adults", *J Am Med Assoc.* 2006; 295:50-57). Multiple reentrant circuits contribute to the VF waveform causing its pathophysiology to be extremely dynamic. A victim's chances of survival worsen by 10% for every minute of VF that remains untreated (cf. T. D. Valenzuela, D. J. Roe, S. Cretin, D. W. Spaite, and M. P. Larsen, "Estimating effectiveness of cardiac arrest interventions: a logistic regression survival model", *Circulation.* 1997; 96: 3308-3313). Defibrillation is a procedure that delivers an electrical current that depolarizes a critical mass of the myocardium simultaneously. Defibrillation increases the possibility of the sino-atrial node regaining control of the rhythm. Coronary artery perfusion provided by cardio-pulmonary resuscitation (CPR) prior to defibrillation has been shown to improve chances for return of spontaneous circulation (ROSC). As victims enter the CPR phase of cardiac arrest, predicting defibrillation success may become paramount to prevent unnecessary interruptions to CPR (cf. M. L. Weisfeldt and L. B. Becker, "Resuscitation after cardiac arrest: a 3-phase time-sensitive model", *J Am Med Assoc.* 2002; 288 (23)3008-13). Repetitive unsuccessful shocks can reduce chest compression time and can cause injury to cardiac tissue, impacting heart function upon survival. Even worse, unsuccessful shocks can cause VF to deteriorate into asystole or pulseless electrical activity (PEA), which are more difficult to resuscitate (cf. H. Strohmenger, "Predicting Defibrillation Success", *Cardiopulmonary Resuscitation*, 2008; 14:311-316).

The effect of acute ischemia on tissue excitability induces conversion of VF from type-1 coarse VF to type-2 smooth VF (cf. A. V. Zaitsev, O. Berenfeld, S. F. Mironov, J. Jalife, and A. M. Pertsov, "Distribution of excitation frequencies on the epicardial and endocardial surfaces of fibrillating ventricular wall of the sheep heart", *Circ Res.,* 2000; 86:408-417). Type 1 VF has now been correlated with the multiple-wavelet theory, while type-2 has been shown to be driven by a mother rotor (cf. J. N. Weiss, Z. Qu, P. S. Chen, S. F. Lin, H. S. Karagueuzian, H. Hayashi, A. Garfinkel, and A. Karma, "The Dynamics of Cardiac Fibrillation", *Circulation,* 2005; 112: 1232-1240). This conversion partially conforms to rapidly attenuating chances of survival with increasing VF duration (cf. J. Eilevstjonn, J. Kramer-Johansen, and K. Sunde, "Shock outcome is related to prior rhythm and duration of ventricular fibrillation", *Resuscitation,* 2007, 75: 60-6), and can be quantified by any measure that can account for both, a decrease in amplitude and a shift in spectral composition of the signal. Fourier Transform (FT) based measures (cf. G. Ristagno, A. Gullo, G. Berlot, U. Lucangelo, F. Geheb, and J. Bisera, "Prediction of successful defibrillation in human victims of out-of-hospital cardiac arrest: a retrospective electrocardiographic analysis", *Anaesth Intensive Care* 2008; 36: 46-50) assume a linear, deterministic basis for the signals, and prove to be impracticable. Other methods (cf. J. N. Watson, N. Uchaipichat, P. S. Addison, G. R. Clegg, C. E. Robertson, T. Eftestol T, and P. A. Steen, "Improved prediction of defibrillation success for out-of-hospital VF cardiac arrest using wavelet transform methods", *Resuscitation* 63: 269-275, 2004, and A. Neurauter, T. Eftestøl, and H-U. Strohmenger. "Prediction of countershock success using single features from multiple ventricular fibrillation frequency bands and feature combinations using neural networks", *Resuscitation* 73, 253-263, 2007), with somewhat more feasible definitions of post-shock success, have focused on creating predictive models based on the real Discrete Wavelet Transform (DWT). While wavelet decomposition has proven to be more effective, clinical transition of such approaches has been precluded due to low specificities.

Gundersen and colleagues (cf. K. Gundersen et al, "Identifying approaches to improve the accuracy of shock outcome prediction for out-of-hospital cardiac arrest", *Resuscitation*. Volume 76, Issue 2, February 2008, Pages 279-284) have shown that predictive features of the VF waveform suffer from random effects, with p-values less than 10-3. This was proved with a mixed effects logistic regression model. Random effect-sizes, calculated as standard deviation of the "random" term in the model, varied from 73% to 189% of the feature effect-sizes. Thus an additional objective of our work aims at countering the variance due to such effects. We hypothesized that other physiologic signals obtained during CPR, such as end-tidal carbon dioxide ($PetCO_2$), can help build a more "complete" model.

SUMMARY OF THE INVENTION

Several physiologic signals are monitored during the resuscitation of the victims of cardiac arrest. The most common of these include electrocardiogram (ECG). Others, however, can be monitored although there is variation among practitioners. These may include but not limited to end-tidal CO2 ($ETCO_2$), blood pressure, impedance, airway pressure, central venous oxygen saturation, etc. In addition, more signals may be monitored during the post-resuscitation period after return of spontaneous circulation (ROSC).

The ECG signal of VF has been analyzed for certain characteristics which may be predictive of successful defibrillation but to date no analytical technique has been widely accepted. We develop a unique approach of computational VF waveform analysis, with and without addition of the signal of end-tidal carbon dioxide ($ETCO_2$), using advanced machine learning algorithms.

According to the present invention, ECG signals are analyzed and features are extracted in the (original) time-domain, with a non-linear non-deterministic method named RPD-PD, and Dual-Tree Complex Wavelet Transform. Features are then selected with a cost-sensitive SVM ranking and a modified wrapper approach for subset selection. Upon selection of features, a parametrically optimized support vector machine (SVM) model was trained with radial basis function kernel for predicting outcomes on the test sets. Training and testing was performed with nested 10-fold cross validation and 6-10 features for each test fold. The approach allows incorporation of a diverse number of physiologic signals, which can be collected during cardiopulmonary resuscitation attempts and in the post-resuscitation period to help guide therapy and predict decompensation.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE INVENTION

The "QRS" complex represents ventricular depolarization (contraction), with Q and S representing minima, while R represents a maximum in the ECG waveform. Lack of a clear QRS complex renders traditional methods of ECG analysis, which use physiologic correlates of the detected P, R and T waves, ineffective. Furthermore, during VF, there are continuous variations in amplitude, axis and morphology of the ventricular baseline.

A "feature" can be any measure from the raw or modified/filtered/transformed data that is indicative of the underlying physiology/characteristics of the system. We conjectured that factors which can affect shock outcome may be explored by modeling the data through non-linear methods, as well as, by deriving more general statistical measures of the pre-shock signal-segment in multiple domains. Counter to our experience (cf. S. Shandilya, S. Y. Ji, K. R. Ward, and K. Najarian, "Prediction of Shock Outcome Using Signal Processing Machine Learning", *Circulation*, 122:A242, 23, November 2010), previous efforts to combine multiple features (cf. A Neurauter, T Eftestøl, and H-U Strohmenger. "Prediction of countershock success using single features from multiple ventricular fibrillation frequency bands and feature combinations using neural networks", *Resuscitation* 73, 253-263, 2007) have failed to improve algorithmic performance.

Figure 1:
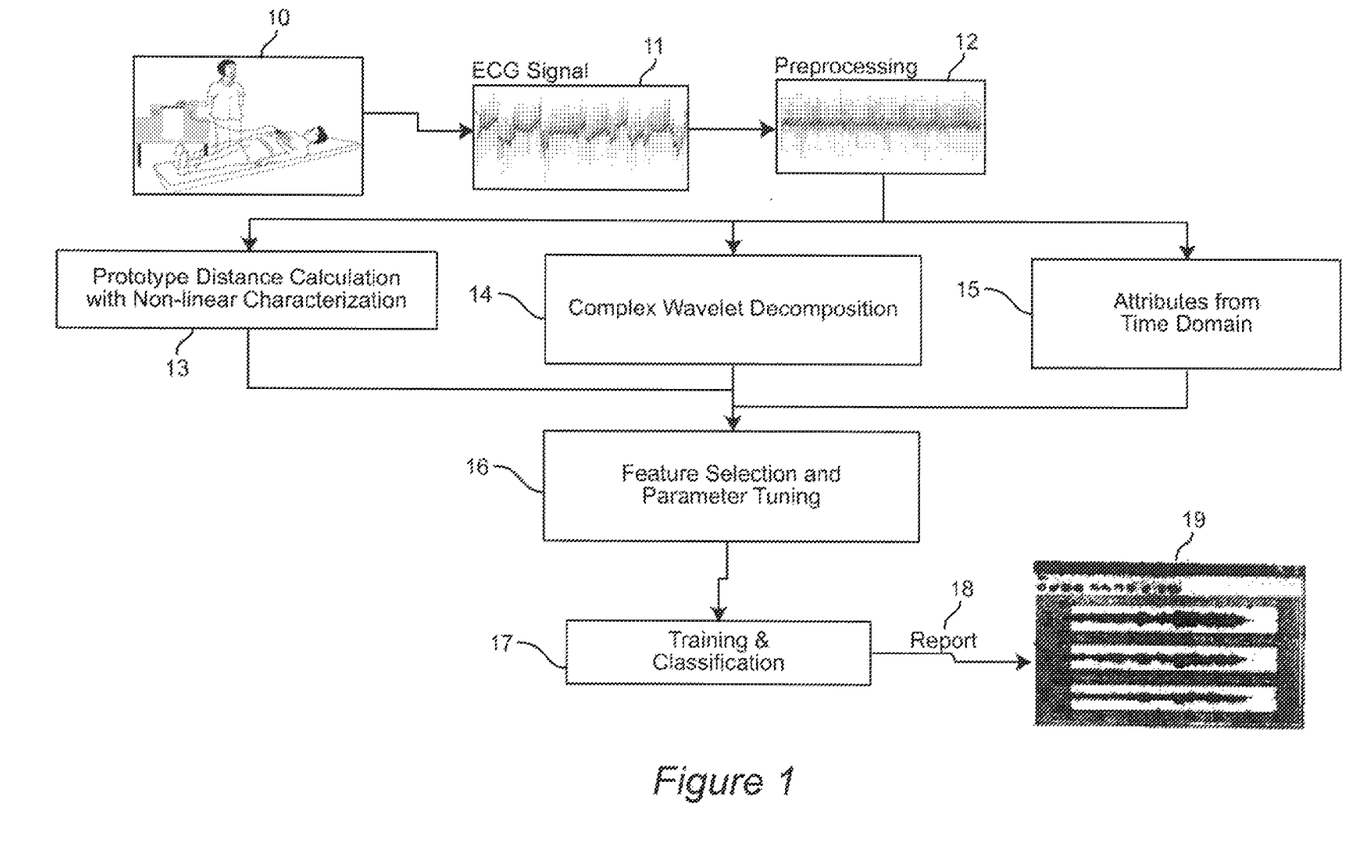
FIG. 1 is a system block diagram showing of the Decision Support System which implements the method according to the invention.

Referring now to the drawings, and more particularly to FIG. 1, there is illustrated a block diagram of the Decision Support System which implements the integrative model that performs real-time, short-term analysis of ECG through machine learning techniques according to the invention. Block 10 represents a patient with attached electrodes of an ECG machine. The output of the ECG machine is an ECG signal at 11, and this ECG signal is subjected to preprocessing at 12. The preprocessed signal is then input to multiple signal processing blocks. These include a prototype distance calculation with non-linear characterization block 13, a complex wavelet decomposition block 14 and an attributes from time domain block 15. The outputs of each of these signal processing blocks are input to a feature selection and parameter tuning block 16, the output of which is input to a machine training and classification block 17. This block outputs a report 18 which is displayed on a suitable display device 19.

Figure 2:
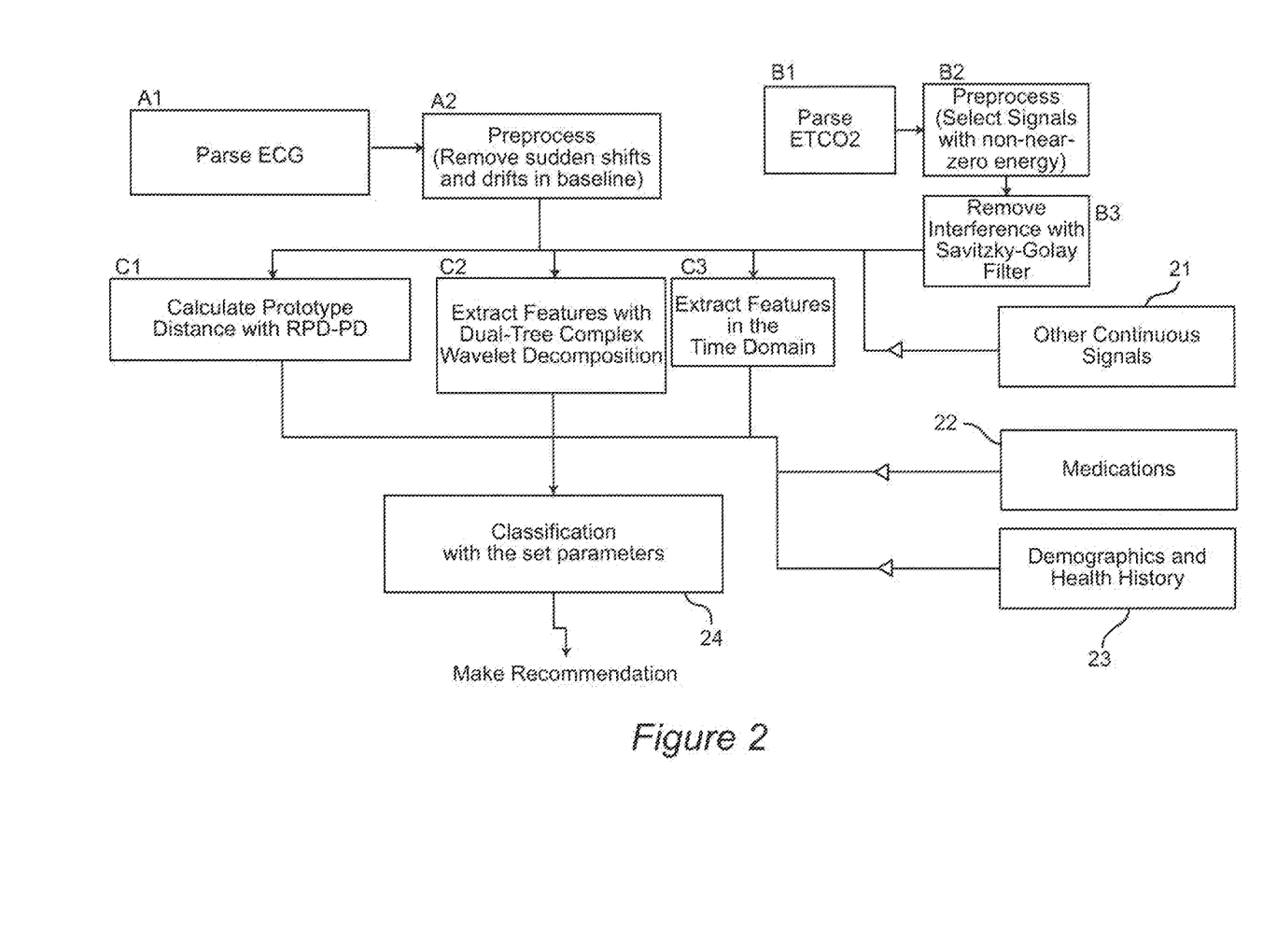
FIG. 2 is a block diagram showing the overall real-time system including signal processing of the ECG and $ETCO_2$ signals and other inputs.

FIG. 2 provides an overview of the real-time system. The first step at block A1 is to parse the ECG signal. Then, in block A2, the ECG signal is preprocessed by removing sudden shifts and drifts. Simulataneously, the ETCO2 signal is parsed at block B1, and this signal is preprocessed in block B2 by selecting signals with non near-zero energy. Then, in block B3, interference is removed with a Savitsky-Golay filter. Signals from blocks A2 and B3 and other continuous physiologic signals 21 are input to the next series of blocks. The other continuous physiologic signals by be tissue impedance, vascular waveform data, tissue oxygenation signals from near infrared spectroscopy and other tissue oxygenation devices. More particularly, in block C1 the prototype distance is calculated with RPD-PD. In block C2, features are extracted with duel-tree complex wavelet decomposition. In block C3, features are extracted in the time domain. The outputs of each of blocks C1, C2 and C3, together with information on the patient's medications 22 and demographics and health history 23 to the classification block 24. Classification is made with set parameters, and a recommendation is output.

Figure 3:
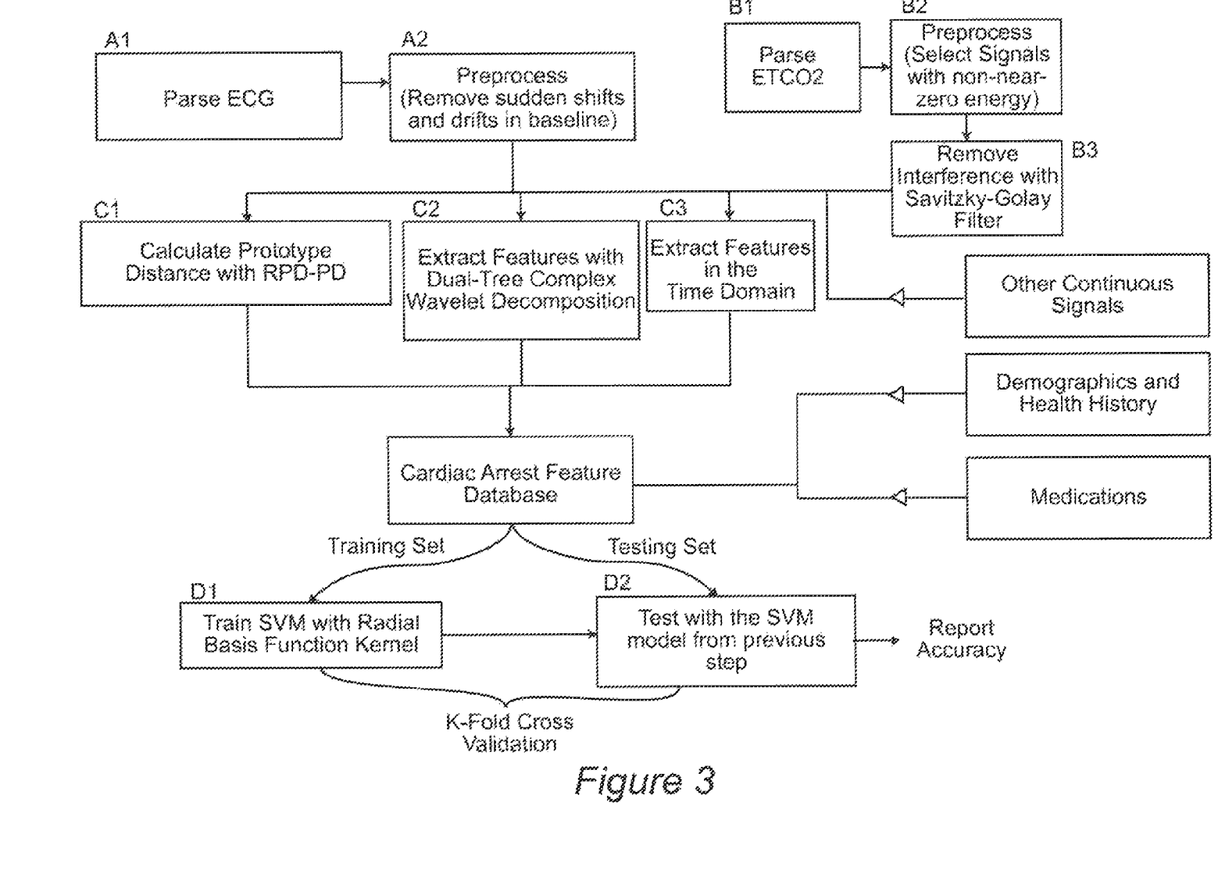
FIG. 3 is a flow diagram showing the training and decision support processes for a targeted optimized resuscitation task.

FIG. 3 illustrates the high level steps of the invention. De-identified cardiac arrest data, for a total of 57 subjects from a data bank were included in a study conducted for assessment and validation of the method according to the invention. See block A1 in FIG. 3. Prior to computational analysis, shocks were manually classified as either successful or unsuccessful based on the post-defibrillation ECG segments and data from the pre-hospital care record. Successful defibrillation was defined as a period of greater than 15 seconds with narrow QRS complexes under 150 beats per minute with confirmatory evidence from the medical record or ECG that a return of spontaneous circulation (ROSC) has occurred. Such evidence included lack of CPR resumption over the next minute, mention of ROSC in record, and/or rapid elevation in PetCO2 levels. While others have utilized alternative definitions that incorporate longer periods of ROSC and specific blood pressures, we chose this definition because a shorter timeframe is more clinically relevant in light of a renewed emphasis on minimizing "hands-off" time during the CPR duty cycle as well as the ever evolving treatment paradigms of cardiac arrest (cf. Berg et al. "Part 5: Adult Basic Life support: 2010 AHA guidelines for Cardiopulmonary Resuscitation and Emergency Cardiovascular Care", *Circulation* 2010; 122; S685-S705). The short pause allows for ROSC determination and rapid return to CPR if defibrillation was unsuccessful. A total of 90 counter shocks were analyzed (56 unsuccessful and 34 successful).

Where available, $ETCO_2$ data obtained from capnography was also parsed from the subjects' records. See block B1 in FIG. 3. $ETCO_2$ monitoring allows for the measurement of exhaled carbon dioxide from a patient. The level of exhaled carbon dioxide has been positively correlated with the amount of blood flow produced by chest compressions during. $ETCO_2$ values for a total of 48 pre-defibrillation signal-segments were used to extract features that could be valuable in predicting the success of a defibrillation in terminating VF, leading to ROSC.

The technique proposed in Shandilya et al (cf. S. Shandilya, M. C. Kurz, K. R. Ward, and K. Najarian, "Predicting defibrillation success with a multiple-domain model using machine learning", *IEEE Complex Medical Engineering.* 2011, 22-25) was used to process the signals for further analyses. Some signals exhibited high frequency noise, which was attenuated by application of the Savitzky-Golay low-pass (smoothing) filter (cf. A. Savitzky and M. J. E. Golay, "Smoothing and Differentiation of Data by Simplified Least Squares Procedures", *Anal. Chem.*, July 1964, 36 (8): 1627-1639). High-frequency attenuation was achieved by fitting a moving window, of width k data points, to a p≤k−1 degree polynomial by the least-squares method. For a constant p, k is set to be relatively small when only "slight" smoothing is needed; thereby making the difference between p and k to be relatively small as well. Simple averaging filters were avoided so as to better preserve the high-frequency content.

Figure 4:
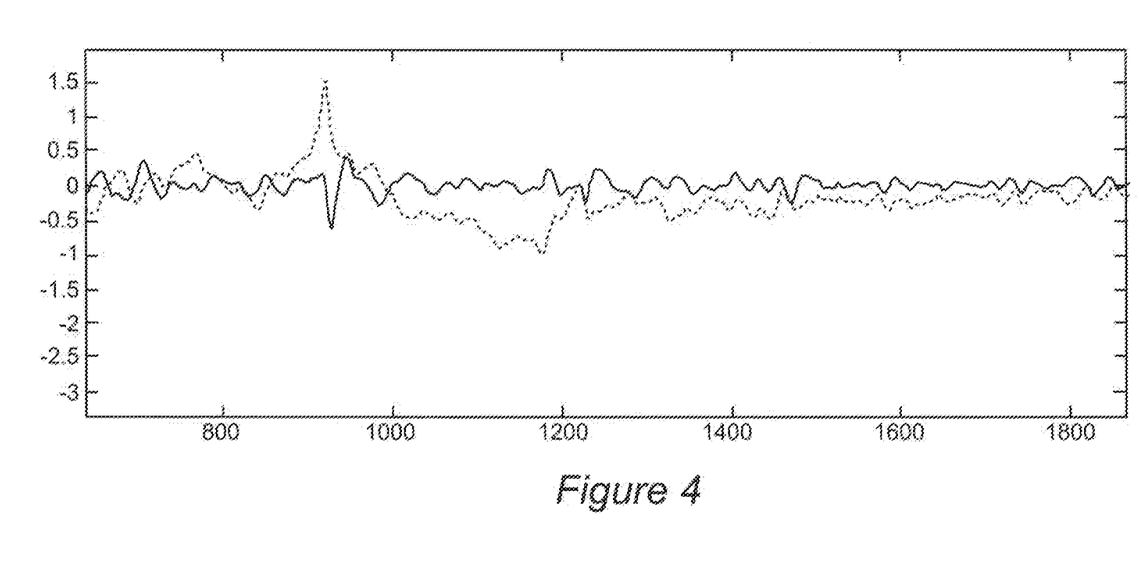
FIG. 4 is a graphical representation of the removal of drifts and sudden shifts in the ECG signal.

Next, sudden baseline jumps and drifts caused by interference were removed, as illustrated in FIG. 4. The signal was successively "smoothed" by repetitive application of Savitzky-Golay filter until only the jumps and drifts remained. The resulting signal was then subtracted from the already "low-passed" signal obtained from the preceding step, yielding the cleaned signal. Frequency-domain dependent filtering methods were precluded due to the presence of all frequencies in a baseline jump and the non-stationary nature of data. Traditional high/low pass filters (such as Butterworth) cannot be employed due to spectral overlap.

Time-series features from block C3 in FIG. 3 are based on a priori reasoning that ROSC yielding VF waveforms exhibit more activity, having properties of the coarser VF, as described above. An illustration of the Pole Count feature (see FIGS. 5A and 5B) depicts the variations in fibrillation activity of the heart along the lead II axis (sampled at 250 Hz) (cf. S. Shandilya, M. C. Kurz, K. R. Ward, and K. Najarian, "Predicting defibrillation success with a multiple-domain model using machine learning", *IEEE Complex Medical Engineering.* 2011, 22-25), and may at least partially represent the extent of homogeneity in VF across classes.

Figure 5A:
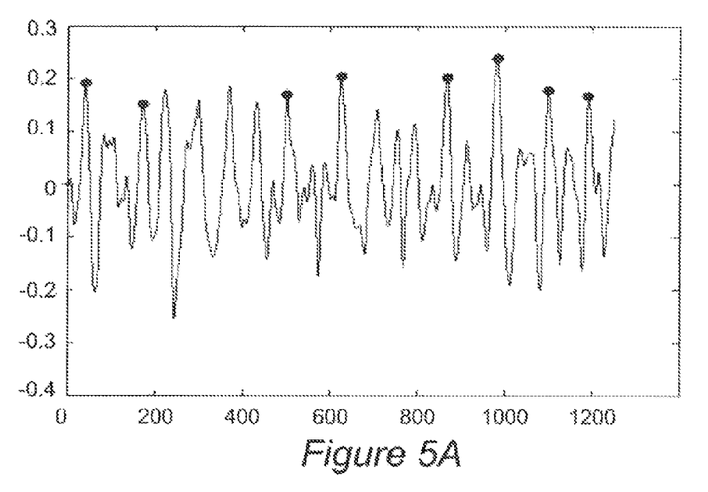
FIGS. 5A and 5B are graphical representations of "pole count" attribute which quantifies variation in the pre-shock waveforms leading to an unsuccessful shock (FIG. 5A) and a successful shock (FIG. 5B)
Figure 5B:
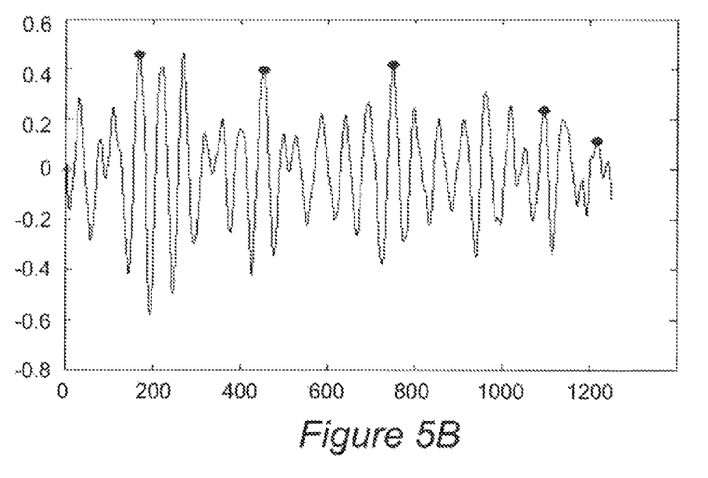

A dynamically adjusting threshold is used to find a minimum number of maxima, Vmx, in the signal. Pole-Count feature is then calculated as the number of maxima that satisfy the following condition:

$$V_{mx}^i > V_{mx}^{i-1} + 1.2 \times \sqrt{\frac{1}{N}\sum_{j=1}^{N}(V_{mx}^j - \overline{V_{mx}})^2} \quad (1)$$

Here, $V_{mx}$ is the vector of all maxima and N is the length of this vector. Next, signal attributes/features are derived from the complex wavelet domain.

Dual-tree complex wavelet decomposition is next performed (see block C2 in FIG. 3). For a signal expressed as a function of time, t, the wavelet transform is described by the following basis set:

$$\phi_{(S,l)}(x) = 2^{-S/2}\phi(2^{-S}t-l) \quad (2)$$

Here, S gives the wavelet's width and l gives its position. The "mother function", Φ, is a decaying wave-like function, altered to form the basis and subject to constraints that all members of the set are orthonormal, which provide a linearly independent set of functions. In Discrete Wavelet Transform (DWT), the scaling function, defined as follows, plays a central role in forming the basis.

$$W(t) = \sum_{k=-1}^{M-2}(-1)^k c_{k+1}\phi(2t+k) \quad (3)$$

where $C_k$'s are the wavelet coefficients, and k and M stand for time-shift and signal length, respectively. Traditional DWT suffers from shift variance. Notably, multiple signal segments (one for each shock) are contributed by each subject. Shift variance can yield spurious features that have false correlations with outcomes. As such, the predictive model generalizes poorly, or put another way, is not discriminative. Complex wavelet decomposition, under certain conditions, can be approximately shift-invariant without a considerable increase in computational complexity for low-dimensional signals; for our case, one-dimensional. Here, the mother function and scaling function, both have a real as well as a complex component.

$$\phi_C(t) = \phi_r(t) + j\phi_i(t) \quad (4)$$

Specifically, when $\Phi_r$ and $\Phi_i$ are Hilbert transform pairs, the decomposition coefficients approach the desired shift-invariant property. This version of Complex Wavelet Transform was implemented using a "dual-tree" decomposition as previously proposed (cf. N. G. Kingsbury, "The dual-tree complex wavelet transform: A new efficient tool for image restoration and enhancement," *Proc. European Signal Processing Conf.*, Rhodes, 1998, 319-322). Multiple attributes were then derived from the resulting coefficients at each level of decomposition, including mean, median, standard deviation, energy and entropy.

Non-linear non-deterministic time-series analysis is next performed (see block C1 in FIG. 3). Fourier Transfer (FT), as utilized by others (cf. G. Ristagno, A. Gullo, G. Berlot, U. Lucangelo, F. Geheb, and J. Bisera, "Prediction of successful defibrillation in human victims of out-of-hospital cardiac arrest: a retrospective electrocardiographic analysis", *Anaesth Intensive Care* 2008; 36: 46-50), performs a linear transformation of a function space such that the original signal (function) is decomposed into multiple sinusoids that are globally averaged. Characterizing a short-term, non-stationary, pathological signal requires the assumptions of linearity and periodicity to be relaxed. Limitations of a Fourier based analysis have also been discussed in other studies (cf. J. N.

Watson, N. Uchaipichat, P. S. Addison, G. R. Clegg, C. E. Robertson, T. Eftestol, and P. A. Steen, "Improved prediction of defibrillation success for out-of-hospital VF cardiac arrest using wavelet transform methods", *Resuscitation* 63: 269-275, 2004, and M. S. Box MS et al., "Shock outcome prediction before and after CPR: A comparative study of manual and automated active compression-decompression CPR", *Resuscitation* 2008; 78:265-274). As with most nonlinear time-series analyses, we begin by projecting our data x(t) onto a state space p(t). Here, each dimension, of the state-space, itself represents a time-delay. The concept of recurrence (cf. H. Kantz and T. Schreiber, *Nonlinear Time Series Analysis*. new edition Cambridge; New York: Cambridge University Press; 1999) can be interpreted as measuring the level of aperiodicity in the data.

$$p(t) \subset \text{hypersphere}(p(t+\delta t), r) \qquad (5)$$

Here, the data projected onto a state-space is p(t), r is the radius of a hypersphere defined around a state p(n) (where n is a specific value of t). Following the data, in state space, δt is the recurrence time at which data falls within the sphere, once again, after having left it. Periodicity is a special case of recurrence when r=0 and all 'states' exhibit the same δ. Time delay embedding is used to project the data series into multiple dimensions of a phase space. Each dimension m corresponds to a multiple of the time delay τ.

$$p_n[P_n, p_{n-\tau}, \ldots, p_{n-(m-1)\tau}] \qquad (6)$$

Autocorrelation and mutual information have been suggested (cf. H. Kantz and T. Schreiber, ibid.) for selecting a proper combination of dimensions m, time delay τ, and radius r. However, our objective is to separate the two classes, "successful" and "unsuccessful", as far as possible based on a distance metric and the given data without losing generalization power. Neither class presents apparently periodic signals. As such, the novel parameter selection regime, as proposed here, finds a "structure" in the signal, defined by dimensions m and time delay e. This structure would differ significantly in its pseudo-periodicities for the two classes. Proper parameter selection is essential in rendering this method useful. Four post-defibrillation signals that exhibited regular sustaining sinus rhythms, with narrow complexes, were selected as successful prototypes. Four defibrillations that induced minimal change in the ECG or were immediately followed by smooth VF, with no conversion, were selected as unsuccessful prototypes. Note that selection of pre-defibrillation signals is "blind" in the sense that only post-defibrillation segments are considered during selection.

For 10-fold cross validation and a dataset with n instances, each training set would contain n−(n/10) samples, thus leaving out the test set. A range of possible values was defined for each parameter. Recurrence period density was then calculated for each combination of parameter values and each signal in the training-set (TS) and prototype-set (PS). We define the metric KD (Equation 7) to calculate the pairwise distances from each TS density to all PS densities:

$$KD = \sum_{i=1}^{T} (1 + D_i^c) \cdot (D_i^c - D_i^S)^2 \qquad (7)$$

Here, s stands for a given signal while c can stand for any of the other signals; $D^c_i$ and $D^s_i$ are the density values at a certain period i. KD, being inspired by the Kullback-Leibler (KL) distance, is biased towards the characteristics of c but, unlike KL, can also serve to measure the distance between two discrete distributions. Given classes A and B, a density from class A is subdivided into non-overlapping windows or ranges, which are compared (by KD) with respective windows of other densities. Therefore, our optimization is performed over a total of four variables, m, τ, r, and window, as follows.

Classes are maximally separated by maximizing the quantity sep (equation 8). Sep represents closeness of all TS signals to PS signals in their own class (and remoteness from the opposite class), while also accounting for differential variation in within-class distances for the two classes. We deem this normalization necessary, as data in one class may be more homogenous than data in the other.

$$sep = \sum_{i}^{L} \frac{\left(\overline{KD_i^B} - \overline{KD_i^W}\right)}{\max\left(\sqrt{\frac{1}{C^B}\sum_{j=1}^{C^B}\left(KD_i^j - \overline{KD_i^B}\right)^2}, \sqrt{\frac{1}{C^W}\sum_{j=1}^{C^W}\left(KD_i^j - \overline{KD_i^W}\right)^2}\right)} \qquad (8)$$

Here, L is total number of TS instances/defibrillation. For a given i, $KD^B$ and $KD^W$ are means of between-class and within-class distances, respectively, to instances in PS. $C^B$ and $C^W$ are total number of PS instances in the opposite class and i's own class, respectively.

Each input signal from the test set is then compared to each prototype in both classes. The following distance is calculated as two features, $sKD_B$ and $sKD_W$, for a signal s.

$$sKD_{B,W} = \frac{1}{Q}\sum_{p=1}^{Q}\left\{\sum_{i=1}^{T}(1 + D_i^p) \cdot (D_i^p - D_i^S)^2\right\} \cdot \text{sgn}(D^P - D^S) \qquad (9)$$

Here, Q is total number of signals in PS for a given class, T is longest period in the chosen window, $D^P$ and $D^S$ are vectors representing densities of the prototype and s, respectively. The average sKD for each class serves as an attribute of a given signal.

Cross-Validation is frequently employed when there is a limited amount of data available (see blocks D1 and D2 from FIG. 3). Feature selection, performed with cross-validation on the whole dataset, creates a positive bias in prediction accuracies by indirectly using information from the test set. As such, feature selection must be performed within the training set that is generated for each run of k-fold cross-validation. However, using the entire training set leads to overfitting within the training set, which creates a negative bias in accuracies when the test fold is passed through the model Error! Reference source not found (cf R. Kohavi and G. John, "Wrappers for feature subset selection", *Artificial Intelligence*, Vol. 97, pp. 273-324, 1997). To prevent this, and to also select parameters for the learning algorithm in a nested fashion, we employ a twice-nested version of cross-validation (FIG. 2).

A "best performing" feature subset can be defined as one that leads to the highest average (cross-validated) accuracy for a given nested run. Traditionally, either a subset that performs best for the greatest number of nested/inner runs is chosen (thereby, partially accounting for variance or random effects in the data) or, in case where no single subset is chosen for a majority of the inner runs, a union of all chosen subsets (one for each inner run) presumably yields the best performing feature subset for the outermost test fold. Selection-frequencies for each feature were generated as follows.

Figure 6:
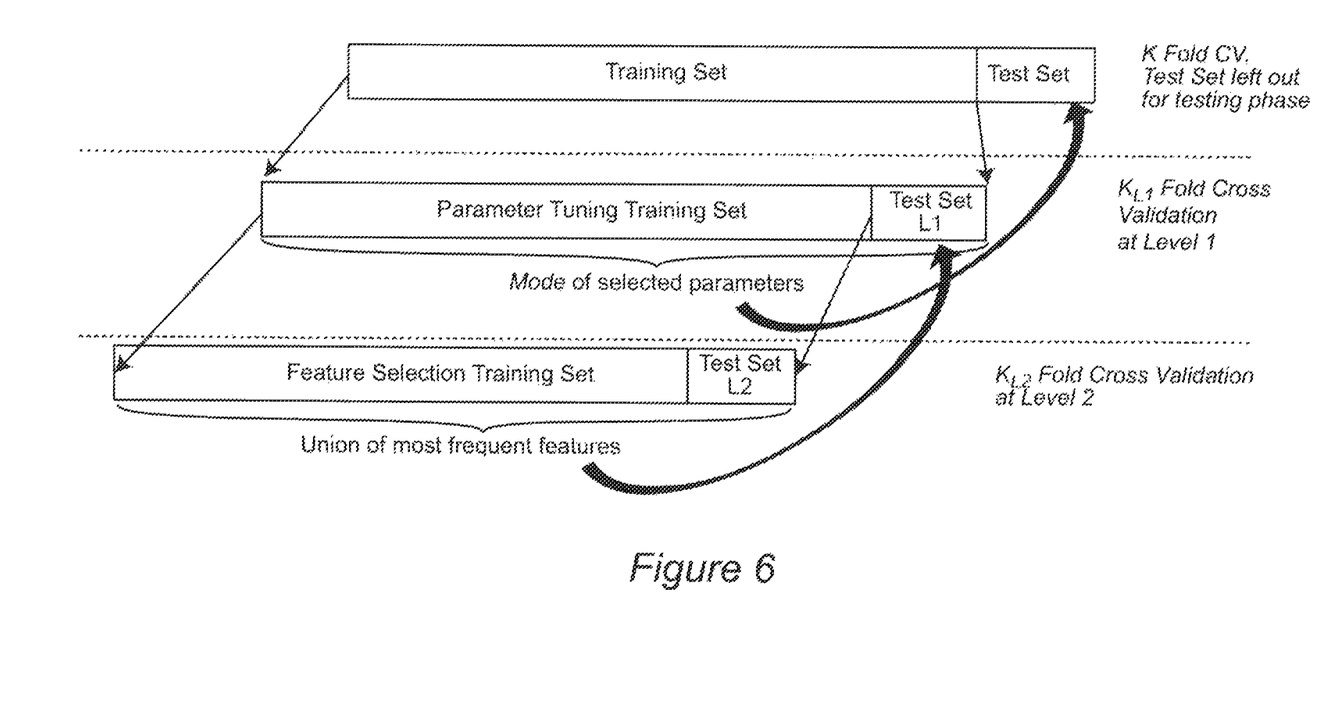
FIG. 6 is a block diagram that illustrates the detailed inner mechanism of block D1 from FIG. 3.

Number of all inner runs, at level 2 (see FIG. 6), for which the feature was selected, divided by (kL1·kL2).

Figure 7:
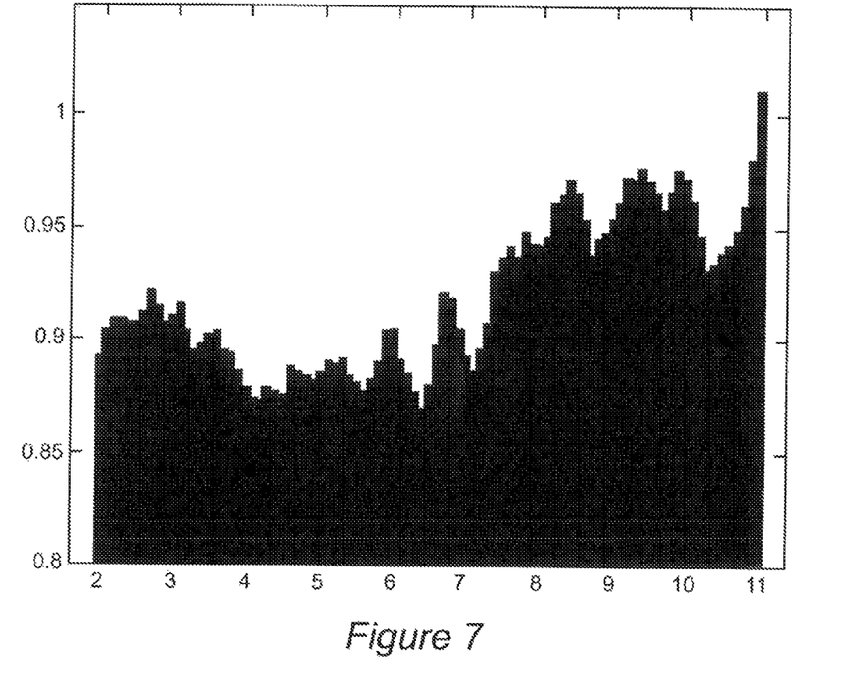
FIG. 7 is a bar plot graphical representation of information content, measured by sep as a function of signal duration in seconds (x-axis)

These frequencies showed that 3 to 5 features were selected for only 20% of the innermost runs, indicating some further room for reduction in model variance by elimination of these spurious features. As an alternative to the traditional "wrapper" approach (cf. R. Kohavi and G. John, ibid.), we formulate a new data matrix with features that were found to be members of the best-performing feature-subsets for at least 70% of the runs (see FIG. 7). This new approach boosted accuracy by approximately 3% without violating blindness to the outermost test folds. The underlying cost-sensitive regime responsible for selecting features for any given training set is as follows.

As our dataset is imbalanced, with unsuccessful to successful ratio of about 2 to 1, classification must be cost-sensitive. However, a cost insensitive approach upstream, i.e. feature selection, may preclude some features that would contribute to a decision boundary strictly between the two classes. In the absence of such features, even cost-sensitive classification yields a decision boundary that is drawn to maximize accuracy only. In order to compensate, false negatives were penalized twice as much as false positives. In other words, feature ranking through RFE-SVMs was done with a 2:1 cost of misclassification.

The feature space was searched by employing Recursive Feature Elimination (RFE) with Support Vector Machines (SVMs) (cf. I. Guyon, J. Weston, S. Barnhill, and V. Vapnik, "Gene selection for cancer classification using support vector machines", *Machine Learning,* 2002; 46:389-422). For a linear SVM, the decision function is given by, $$f(u) = \sum_{k=1}^{n} w_k u_k + b \tag{10}$$

The weight w of each feature, $u_k$, indicates the extent of each feature's contribution to the classifier's continuous output, and n in the total number of features. RFE starts by building a model with all the available features. The one with the smallest |w| is eliminated. At each subsequent step, the model is rebuilt and the elimination is repeated. RFE is similar to Best First Search (BFS) with a backwards approach. In contrast, by using w, we can reduce n runs to 1 run of the classifier at each step in order to eliminate the feature that leads to the smallest decrease in accuracy. Top 9 (n/10) features were then used in the modified wrapper approach described previously. Time-series and complex wavelet features were also extracted from the $PetCO_2$ signal using the exact same methodology as for ECG signals.

G Ristagno, A. Gullo, G. Berlot, U. Lucangelo, F. Geheb, and J. Bisera. "Prediction of successful defibrillation in human victims of out-of-hospital cardiac arrest: a retrospective electrocardiographic analysis", *Anaesth Intensive Care* 2008; 36: 46-50, propose Amplitude Spectral Area (AMSA) as a useful measure for shock outcome prediction. Two important factors contribute to the uniqueness and to the rigor of our problem. Firstly, we seek to perform a VF to VF pre-shock comparison. Secondly, and more importantly, our definition of a successful shock allows an interventionist to monitor the patient's immediate post-shock condition within a reasonable window of time. Ideally this "monitoring interval" would be as small as possible to prevent a negative impact on survival (cf. T. D. Valenzuela, D. J. Roe, S. Cretin, D. W. Spaite, and M. P. Larsen, "Estimating effectiveness of cardiac arrest interventions: a logistic regression survival model", *Circulation.* 1997; 96: 3308-3313). The supervised dataset has to be based on such a definition. No clear AMSA threshold can be identified (FIG. 8) to distinguish successful shocks from unsuccessful ones. Employing a C4.5 (cf. R Quinlan (1993). C4.5: *Programs for Machine Learning*. Morgan Kaufmann Publishers, San Mateo, Calif.) based decision stump or 1-rule for AMSA values yielded 44.1% Sensitivity and 77.2% Specificity. ROC AUC for AMSA was 60.9%. J. N. Watson, P. S. Addison, G. R. Clegg, P. A. Steen, and C. E. Robertson. "Practical issues in the evaluation of methods for the prediction of shock outcome success in out-of-hospital cardiac arrest patients", *Resuscitation.* 2006 January; 68(1): 51-9, and J. N. Watson, N. Uchaipichat, P. S. Addison, G. R. Clegg, C. E. Robertson, T. Eftestol, and P. A. Steen, "Improved prediction of defibrillation success for out-of-hospital VF cardiac arrest using wavelet transform methods", *Resuscitation* 63: 269-275, 2004, have also proven the advantages of a "wavelet" approach over Fourier decomposition. However, the definitions of shock success for the two studies, mentioned above, are similar. Accuracy was calculated as the average percentage of instances, over all cross-validation runs, that were correctly classified. All accuracy, sensitivity and specificity values are reported for the best decision threshold found for the given test and algorithm (see Results).

Figure 8:
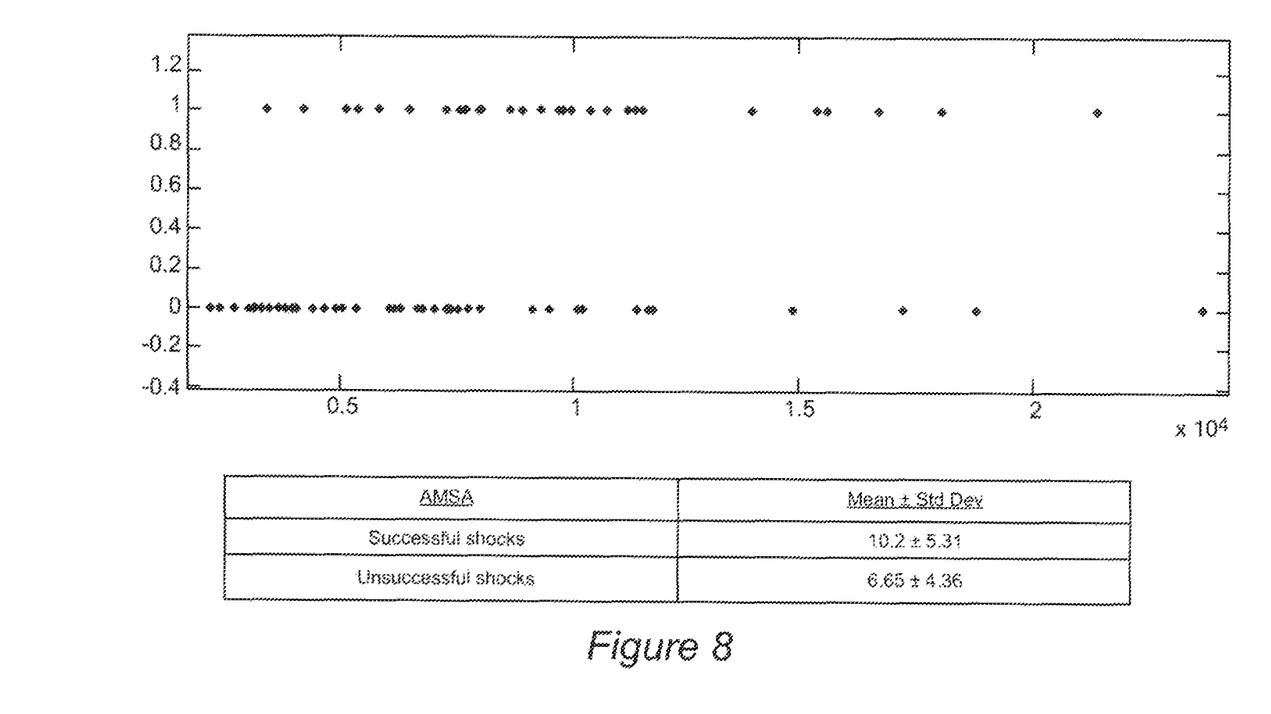
FIG. 8 is a graphical representation of Amplitude Spectral Area (AMSA) which is used as a measure of shock outcome prediction.
Figure 9A:
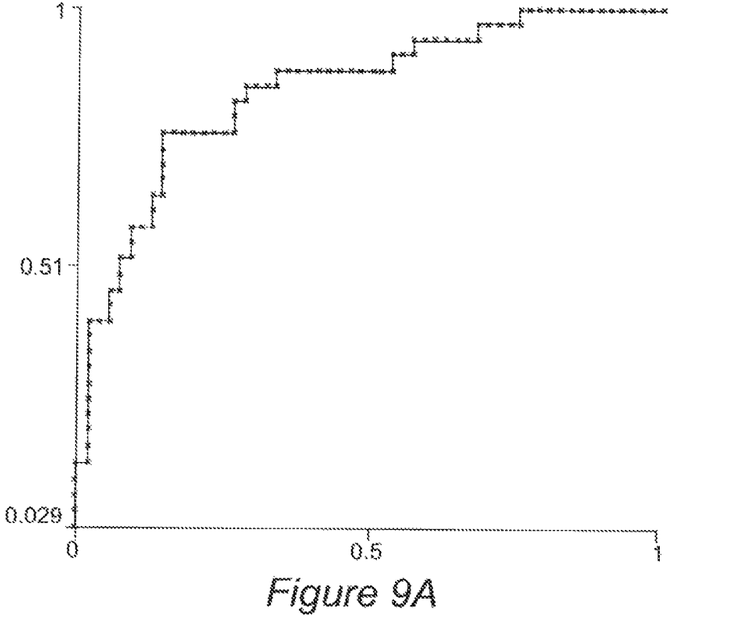
FIGS. 9A and 9B are graphical representations of the receiver operating characteristic curves for the ECG-only based model and the ECG+$ETCO_2$ based model, respectively.
Figure 9B:
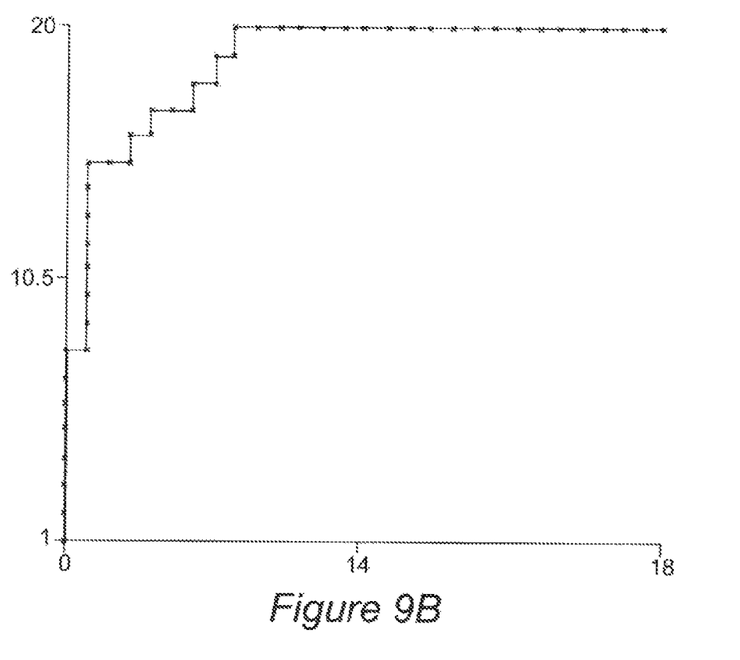

Our algorithm performs in near real-time to output predictions. Receiver Operating Characteristic (ROC, see FIGS. 9A and 9B) curves are used to evaluate reliability of models by calculating the area under the curve (AUC). Classification using our machine-learning approach with 6-10 features yielded an ROC AUC of 85% and accuracy of 82.2%, for the model built with ECG data only (FIG. 8). Integrating PetCO2 features boosted ROC AUC and Accuracy to 93.8% and 83.3%, respectively, for a total of 48 shocks with usable $ETCO_2$ segments. A large ROC AUC allowed for 90% Sensitivity and 78.6% Specificity at a classifier-output threshold value of 0.22. Classifier (support vector machine: SVM) output for each instance is compared to this value before it is assigned to a class. For classification problems, varying this threshold is a common way to assign more weight to one class than the other. The ROC curves were obtained by varying the threshold values between the two classes.

In FIG. 2, the system can identify an optimal physiologic condition for resuscitation by recommending a shock. Alternatively, the invented decision support system can be trained on any segment of the ECG signal, pre or post shock. The ML approach can utilize multiple signals, as demonstrated by the use of $ETCO_2$ and also categorical variables, by simply adopting a different logic (such as decision trees) for the Classification (blocks D1 and D2 in FIG. 3). It is important to note that the feature selection and parameter tuning steps (in FIG. 6) performed on the training cardiac arrest database would still remain in-play with linear-SVMs. As such, when the system is trained with post-successful-defibrillation signals, it would be capable of predicting re-arrest for a patient with ROSC.

In the invented system, therapeutic alternatives and drugs can be used as both, predictors of outcomes as well as the dependent variables, where the system outputs a recommendation for a certain therapeutic approach and/or medication based on the rest of the physiologic signals and categorical data.

Once VF has transitioned into the mother rotor form (cf. A. V. Zaitsev, O. Berenfeld, S. F. Mironov, J. Jalife, and A. M. Pertsov, "Distribution of excitation frequencies on the epicardial and endocardial surfaces of fibrillating ventricular wall of the sheep heart", *Circ Res.*, 2000; 86:408-417), defibrillation should occur as soon as possible. Passage of time, in any pulseless rhythm, is the most significant of survival determinants (cf. J. Eilevstjonn, J. Kramer-Johansen, and K. Sunde, "Shock outcome is related to prior rhythm and duration of ventricular fibrillation", *Resuscitation*, 2007, 75: 60-6 and L. B. Becker, M. P. Ostrander, J. Barrett, and G. T. Kindus, "Outcome of CPR in a large metropolitan area—where are the survivors?", *Ann Emerg Med.*, 1991; 20: 355-361). Effects of VF duration, which may or may not be countered by CPR, can be a pre-determining factor for defibrillation outcome. As such, any feature quantifying the shift in amplitude and frequency content with increasing VF duration may not discern the effects of CPR on outcome. Results derived from such features (cf. G. Ristagno, A. Gullo, G. Berlot, U. Lucangelo, F. Geheb, and J. Bisera, "Prediction of successful defibrillation in human victims of out-of-hospital cardiac arrest: a retrospective electrocardiographic analysis", *Anaesth Intensive Care* 2008; 36: 46-50) can positively bias the perception of any algorithmic analysis' utility during intervention, having implications for studies aiming to predict outcomes of defibrillation attempts during/after chest compressions.

Previous studies (cf. J. N. Watson et al. and A. Neurauter et al., ibid.) have established the advantages of a "wavelet" approach over FT in evaluation of VF. However, their definitions of shock success are similar to that of Ristagno and colleagues (cf. G. Ristagno et al., ibid.). In order to overcome limitations such as the shift variance of traditional DWT, we report a first-use of Complex Wavelet decomposition designed for defibrillation outcome prediction (and for any ECG analysis). Additionally, instead of quantifying the presumably varying degree of aperiodicity across classes through time-delay embedding (cf. M. A. Little, P. E. McSharry, S. J. Roberts, D. A. Costello, and I. M. Moroz, "Exploiting Nonlinear recurrence and Fractal scaling properties for voice disorder detection", *Biomedical Engineering Online*, vol. 6, 2007), RPD-PD separates distributions of frequency content; thereby distinguishing two signals that differ in more ways than just perceived "randomness".

Whenever cross-validation is employed with feature selection or parameter tuning, a twice-nested implementation is requisite for obtaining results that are unbiased by information in the test set. This follows from the assumption that field application will produce previously unseen data, providing a true test for the model. Additionally, there is usually a tradeoff between complexity of the predictive model and its generalization power. As complexity is partly defined by the number of features and values of the machine learning algorithm parameters, nested cross-validation also provides a way to optimize this tradeoff.

While the invention has been described in terms of a single preferred embodiment, those skilled in the art will recognize that the invention can be practiced with modification within the spirit and scope of the appended claims. The advantage of the approach described above is that the techniques can be used to incorporate a rich and diverse suite of other real-time physiologic signals such as those providing information about the status of tissue perfusion other than $ETCO_2$ above. These may include but not be limited tissue perfusion status and signals as measured by bioimpediance methods, tissue oxygenation signals obtained by devices such as near-infrared spectroscopy and other devices, vascular waveform data from vessels obtained by piezoelectric sensors and other devices, etc. Categorical data such as patient demographic information, medical history, patient medication, and medications provided during the resuscitation can be incorporated in the machine learning algorithm and approach described above to provide greater accuracy of predictions. The approach may be used in real time to provide the rescuer feedback in regards to therapy that result in interventions, which lead to indications of a successful resuscitation. Finally, the algorithms and approach using these diverse signal and information input can be used after the patient is resuscitated in order to predict rapid decompensation of the patient that may lead to re-arrest. Predicting this decompensation may allow for interventions which prevent re-arrest.

What we claim is as follows:

1. A computer-implemented method for automated monitoring and online assessment of chances of survival for a patient in cardiac arrest, the method comprising:
    obtaining an ECG signal from the patient;
    preprocessing the ECG signal to remove high frequency noise and baseline jumps caused by noise and interference;
    performing, in a first processor, non-linear characterization of the preprocessed ECG signal and calculating a prototype distance of the preprocessed ECG signal;
    performing, in a second processor, feature extraction of the preprocessed ECG signal with a complex wavelet transform;
    performing, in a third processor, attribute extraction from the preprocessed ECG signal;
    performing, in a fourth processor, attribute extraction from an end tidal $CO_2$ ($ETCO_2$) signal;
    receiving distance values from non-linear characterization of the preprocessed ECG signal, extracted features of the preprocessed time-series ECG signal, attributes extracted from the $ETCO_2$ signal, and attributes extracted from Dual-Tree Complex Wavelet Decomposition of the pre-processed ECG signal, and performing a feature selection using the received data with a predictive model;
    using machine learning to classify results of the feature selection process;
    generating a shock success prediction, which results in return of spontaneous circulation (ROSC);
    generating decompensation and re-arrest prediction; and
    recommending therapeutic alternatives and medications for guiding therapy.

2. The method of claim 1, further comprising integrating categorical data, comprising at least one of demographics, medical history and medication information, into the feature database.

3. The method of claim 1, further comprising performing attribute extraction from other continuous physiologic signals, wherein the continuous physiologic signals comprises at least one of tissue impedance, vascular waveform data from piezoelectric sensors or other devices capable of obtaining vascular waveform data, tissue oxygenation signals from near infrared spectroscopy and other tissue oxygenation devices, and wherein the step of receiving includes receiving attributes extracted from other physiologic signals and categorical variables.

4. A system for automated monitoring and online assessment of chances of survival for a patient in cardiac arrest, the system comprising:
    an ECG device for providing an ECG signal from the patient;
    a filter for preprocessing the ECG signal to remove high frequency noise and baseline jumps caused by noise and interference;

a first signal processor for performing non-linear characterization of the preprocessed ECG signal and calculating a prototype distance of the preprocessed ECG signal;

a second signal processor for performing feature extraction of the preprocessed ECG signal with complex wavelet transform;

a third signal processor for performing attribute extraction from the preprocessed ECG signal;

a fourth signal processor for performing attribute extraction from an end tidal $CO_2$ ($ETCO_2$) signal;

feature extraction means receiving distance values from non-linear characterization of the preprocessed ECG signal, extracted features of the preprocessed time-series ECG signal, attributes extracted from the $ETCO_2$ signal, and the attributes extracted from Dual-Tree Complex Wavelet Decomposition of the pre-processed ECG signal and performing a feature selection using the received data with a predictive model;

a machine learning system for classifying results of the feature selection process, said machine learning system generating a shock success prediction, which results in return of spontaneous circulation (ROSC), generating decompensation and re-arrest prediction, and recommending therapeutic alternatives and medications for, guiding therapy.

5. The system of claim 4, further comprising means for inputting categorical data, comprising at least one of demographics, medical history and medication information, into the feature database of the machine learning system.

6. The system of claim 4, further comprising means for performing attribute extraction from other continuous physiologic signals, wherein the continuous physiologic signals comprises at least one of tissue impedance, vascular waveform data from piezoelectric sensors or other devices capable of obtaining vascular waveform data, tissue oxygenation signals from near infrared spectroscopy and other tissue oxygenation devices, and wherein the extracted attributes from other continuous physiologic signals are input to the machine learning system.

* * * * *